(12) United States Patent
Padros Fradera

(10) Patent No.: US 6,340,300 B1
(45) Date of Patent: Jan. 22, 2002

(54) DENTAL IMPLANT

(75) Inventor: Alejandro Padros Fradera, Barcelona (ES)

(73) Assignee: Soadco, S.L., Escaldes-Engordany ( * ) Notice: Subject to any disclaimer, the term of this patent is extended or adjusted under 35 U.S.C. 154(b) by 0 days.

(21) Appl. No.: 09/653,160

(22) Filed: Sep. 1, 2000

(30) Foreign Application Priority Data

Oct. 6, 1999 (ES) .............................. 9902521 U

(51) Int. Cl.[7] ................................................ A61C 8/00
(52) U.S. Cl. ........................................ 433/174; 433/173
(58) Field of Search ................................ 433/172, 173, 433/174, 175, 176

(56) References Cited

U.S. PATENT DOCUMENTS 5,169,309 A * 12/1992 Staubli et al. .............. 433/173
5,417,692 A * 5/1995 Goble et al. ................ 433/173
5,816,809 A * 10/1998 Sapkos ....................... 433/172

* cited by examiner

*Primary Examiner*—John J. Wilson
(74) *Attorney, Agent, or Firm*—Sughrue Mion, PLLC

(57) ABSTRACT

It is composed of an elongated cylindrical titanium body, intended for implanting in a jawbone and provided, at its outer end, with a frusto-conical coaxial portion (3), the larger outer base of which has a prismatic polygonal protuberance (5), whose lateral sides (8) are adapted to be joined to external mechanical elements by way of key.

The outer surface of prismatic protuberance (5) is fitted with an outward tubular extension (6), coaxial to the main body, provided with a central hole (10) which allows the fixing screw to be threaded through and whose outer surface (8) is provided with threads adapted to receive the threading of an inner threading formed on the base of a preprosthetic cap, provided with a through hole which allows the fixing screw to go through from the prosthesis to the implant.

2 Claims, 1 Drawing Sheet

DENTAL IMPLANT

TECHNICAL SECTOR OF THE INVENTION

The invention refers to a self-tapping dental implant of the type which are fitted into the jawbone and are used as a base for fixing dental prostheses.

BACKGROUND TO THE INVENTION

It is well-known that the positioning of a dental prostheses is done by means of the prior fixing of a dental implant to the upper jawbone or to the lower jawbone which, once its proper integration into the bone has been tested, is used as a base for fixing the prosthesis.

More particularly, screw-type dental implants are known which, in synthesis, are composed of a generally cylindrical main body, with an external threading to be threadedly attached into the upper or lower jawbone, the main body being obtained from metallic material, preferably titanium. On the outer end of said main body a frusto-conical part is preferably positioned, the smaller base of which links to said threading, while its larger base extends into a prismatic protuberance, preferably hexagonal in cross-section, provided with threaded axial hole, said protuberance permitting the threading of the main body by means of a tool, such as a key. Once the dental implant is positioned in its definitive location, a threaded preprosthetic cap has to be fitted to the prismatic protuberance, said cap allowing a threaded screw to be passed through joining the implant to the dental prosthesis.

The dental implants previously described can be fitted to a patient in two distinct ways, the first of which consists of making the perforation in the upper jawbone or lower jawbone with a specially designed tool threading the perforated hole by means of a tapping device or the like and afterwards fitting the dental implant into its definitive position inside the preformed perforation; the other way of fitting the implant consists of using the implant itself as a tool to thread the inside of the hole made in the jawbone by removably coupling a suitable tool to it to make the implant turn and push it downwardly, with which the implant remains in its definitive position when the perforation has finished and thus avoiding an intermediate operation.

This second method considerably reduces the time required to fit the implant, relieving the patients discomfort as a result. Dental implants which are used as threading or tapping tools are commonly known as self-tapping implants.

Self-tapping dental implants of the type previously described have the drawback that the edges of the lateral sides of the prismatic protuberance undergo a rapid deterioration when the mechanical outer element, with all the necessary force to screw the upper or the lower jawbone, is directly applied to it, due to the implants having to be of titanium, which is a soft metal.

The deterioration of these edges of the lateral sides prevents the adequate fixing of the preprosthetic cap to the implant, once the latter is placed in its definitive position, with which the base, where the fixing screw must remain perfectly fixed is not well engaged to the implant either, wherefore the joining between the implant and the prosthesis is not rigid enough.

EXPLANATION OF THE INVENTION

A newly structured dental implant has been created with the object of providing a solution to the problems previously described deriving from the deterioration of the edges of the lateral sides of the surface in which the preprosthetic cap is screwed in, due to the significant force necessary to apply on surfaces which are later used as a base for the fixing of dental prostheses by using the implant itself as a tool to perforate the jawbone and, despite of the fact it does not avoid the wearing away of the edges of the prismatic protuberance, it prevents the deterioration of the threading designed for gripping the preprosthetic cap to the implant.

The self-tapping dental implant object of the present invention is of the type described earlier and is characterized essentially in that the outer surface of the protuberance is fitted with an outward tubular extension, coaxial to the main body, provided with a central hole which allows the fixing screw to be threaded through and whose outer surface is provided with a threading which is adapted to receive the threads of an inner threading formed on the base of a preprosthetic cap provided with a through hole which allows the fixing screw to go through from the prosthesis to the implant, all of it adapted in such a way that the preprosthetic cap is adapted to be fixed solidly by threading to said tubular extension, also covering the protuberance, without the need for any additional screw.

In accordance with another feature of the present invention, between the prismatic protuberance and the truncated frusto-conical portion, a frusto-conical section if provided, of a low and an inverse conicity to that of the previous frusto-conical section, the larger bases of which coincide and are opposite one another.

The features of the dental implant described earlier, provide a solution to the previously mentioned drawbacks which the carrying out of the known self-tapping dental implants have.

With the self-tapping dental implant object of the present invention, even though it does not prevent the deterioration of the edges of the prismatic protuberance, the force applied to the implant is optimized, at the same time managing to keep the threading of the tubular extension intact for the precise fitting of the preprosthetic cap.

BRIEF DESCRIPTION OF THE DRAWINGS

In the appended drawings a preferred form of embodiment the dental implant object of the present invention is represented, by way of non-limiting example. In said drawings.

DETAILED DESCRIPTION OF THE DRAWINGS

In said drawings the different parts forming the implant can be made out.

Figure 1:
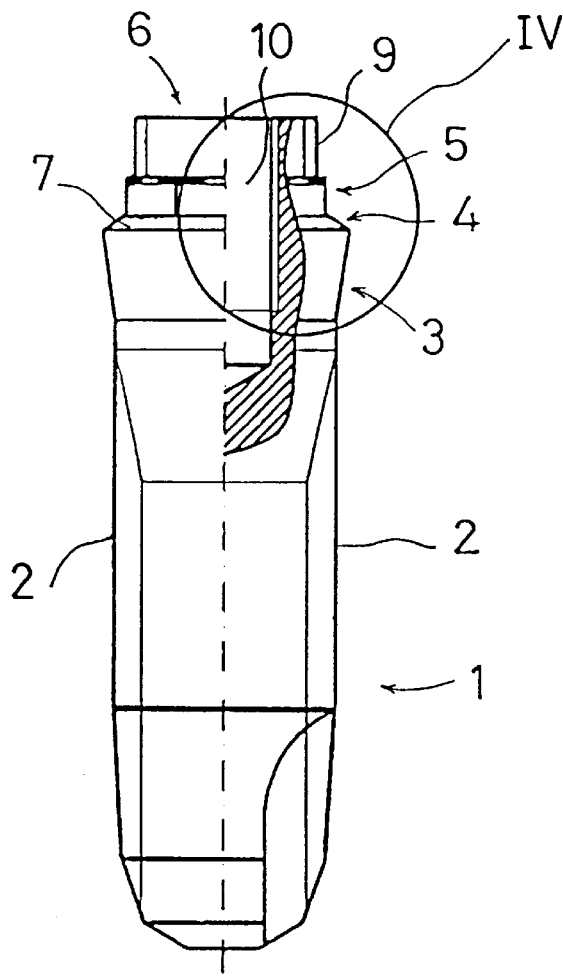
FIG. 1 is an elevation view, in partial section, of the dental implant object of the present invention.

As is shown in FIG. 1, the implant has an essentially elongated cylindrical shape and comprises a first inner cylindrical portion 1, whose outer surface 2 shows a threading, which extends its entire length allowing it to be fixed to the upper jawbone by threading.

Following said cylindrical portion 1 there are: a second coaxial frusto-conical portion 3; a third coaxial frusto-conical portion 4; a prismatic protuberance 5, coaxial and hexagonally cross-sectioned, arranged on the smaller base of said frusto-conical portion 4; and finally, on the outermost part, a tubular extension 6 towards the outside.

The viewed surface 7 of frusto-conical portion 4 fulfills two very important functions: a first function consists of allowing the most precise adaptation possible of the mechanical tool to be used when it is necessary to put uniform pressure on the implant for a correct threading of the jawbone hole into which it is inserted and a second function, which is that of being used as a resting base of the preprosthetic cap (not shown), when the latter is threaded to tubular extension 6.

Outer surface 8 of tubular extension 6 is equipped with a threading 9, adapted to receive the fitting by threading of a pre-prosthetic cap, which has not been represented.

Tubular extension 6 is provided with a centrally arranged hole 10, which extends through the entire height of protuberance 5, of frusto-conical portion 4 and of frusto-conical portion 3, until reaching cylindrical portion 1, in which it penetrates a relatively reduced distance.

Threaded hole 10 is adapted to receive a fixing screw (not shown) which will fulfill the engaging function between the implant and the dental prosthesis.

Figure 2:
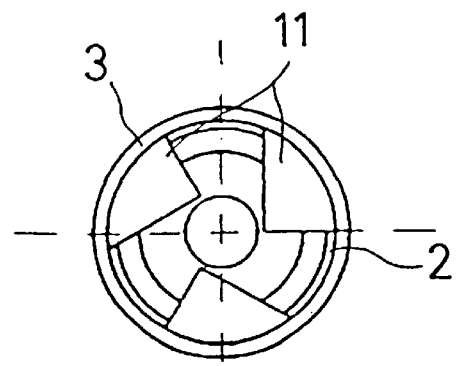
FIG. 2 shows a bottom plan view of the implant of the view in FIG. 1.

FIG. 2 shows the cutting edges 11 situated in the innermost part of the first cylindrical portion 1 of the self-tapping dental implant. The cutting edges 11 perforate the jawbone as a reaction to the inward pressure of the bone and to the rotating movement performed by the outer mechanical tool.

Figure 3:
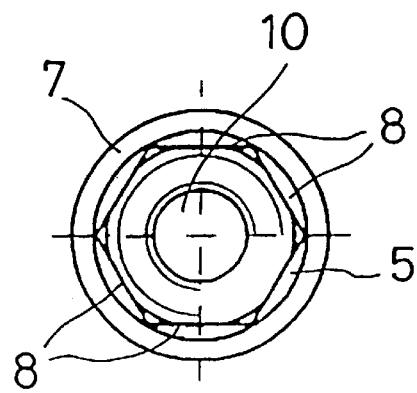
FIG. 3 is a top plan view of the implant in FIG. 1.
Figure 4:
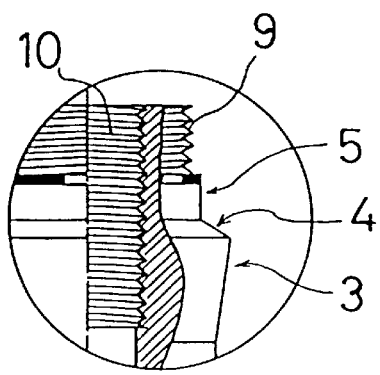
FIG. 4 is a view of detail IV in FIG. 1.

In FIG. 3 the central threaded hole 10 can be made out, into which a fixing screw will be screwed in at a later stage.

The straight prismatic protuberance 5 of a hexagonal cross-section, is placed between tubular extension 6 and truncated cone-shaped part 4, with each of its lateral sides adapted to receive the fitting of an external mechanical tool which puts pressure on surface 7, at the same time causing a rotating movement in order to insert the implant in the jawbone by threading the preformed hole in same.

What is claimed is:

1. Self-tapping dental implant, of the type which is fixed into the upper jawbone, is used as a base for fixing dental prostheses and includes an elongated, cylindrical main body, provided with an external screw thread, of a metallic material for implanting in a jawbone and provided, at its outer end, with a frusto-conical portion (3), a larger outer base of which has a protuberance (5) of relatively reduced height and an essentially straight prismatic polygonal cross-section, said frusto-conical portion being coaxial to the main body and being provided with a threaded central coaxial hole (10) adapted to receive a fixing screw of a dental prosthesis, the lateral sides (8) of the prismatic protuberance (5) being adapted to be engaged by a tool for threading the implant into a preformed hole on the upper or lower jawbone, characterized in that the outer surface of said prismatic protuberance (5) has an outward tubular extension (6), coaxial to the main body, and provided with a hole aligned with the central hole (10) which allows the fixing screw to pass through and has an outer surface (8) which is provided with external threads (9) adapted to receive the threads on an inner surface of a base of a pre-prosthetic cap which is also, provided with a through hole which allows the fixing screw to pass through from the prosthesis to the implant, wherein the pre-prosthetic cap is adapted to be fixed solidly by threading onto said external threads (9) on said tubular extension (6) and covering the protuberance (5) without the need for any additional screw.

2. Self-tapping dental implant in accordance with claim 1 characterized in that, between the prismatic protuberance (5) and the frusto-conical portion (3) a frusto-conical portion (4) is arranged, of a low height and of an inverse conicity to that of the frusto-conical portion (3), the larger bases of which coincide and are opposite one another.

* * * * *